(12) United States Patent
Faram

(10) Patent No.: US 9,849,254 B2
(45) Date of Patent: Dec. 26, 2017

(54) PRE-FILLED, SMALL-VOLUME NEBULIZER

(75) Inventor: Joseph Dee Faram, Dallas, TX (US)

(73) Assignee: Caddo Medical Technologies LLC, Dallas, TX (US)

( * ) Notice: Subject to any disclaimer, the term of this patent is extended or adjusted under 35 U.S.C. 154(b) by 1494 days.

(21) Appl. No.: 11/748,907

(22) Filed: May 15, 2007

(65) Prior Publication Data

US 2008/0283050 A1    Nov. 20, 2008

(51) Int. Cl.
| | |
|---|---|
| *A61M 11/02* | (2006.01) |
| *A61M 15/00* | (2006.01) |
| *A61M 11/00* | (2006.01) |
| *A61M 11/06* | (2006.01) |

(52) U.S. Cl.
CPC ........ *A61M 11/02* (2013.01); *A61M 15/0003* (2014.02); *A61M 15/004* (2014.02); *A61M 15/0016* (2014.02); *A61M 11/00* (2013.01); *A61M 11/06* (2013.01); *A61M 2205/123* (2013.01)

(58) Field of Classification Search
USPC ............ 128/200.14, 200.21, 200.24, 203.21, 128/204.14, 205.21, 205.23, 913; 239/339
See application file for complete search history.

(56) References Cited

U.S. PATENT DOCUMENTS

| | | | |
|---|---|---|---|
| 2,726,896 A * | 12/1955 | McKinnon .............. | 239/335 |
| 3,774,602 A * | 11/1973 | Edwards ............. | 128/200.16 |
| 3,945,378 A | 3/1976 | Paluch | |
| 4,036,919 A | 7/1977 | Komendowski et al. | |
| 4,150,071 A * | 4/1979 | Pecina .................. | 261/78.2 |
| 4,253,468 A | 3/1981 | Lehmbeck | |
| 4,534,343 A | 8/1985 | Nowacki et al. | |
| 4,595,002 A | 6/1986 | Michaels et al. | |
| 4,657,007 A * | 4/1987 | Carlin et al. .......... | 128/200.18 |
| 4,951,661 A * | 8/1990 | Sladek ................. | 128/202.27 |
| 5,209,225 A * | 5/1993 | Glenn ................... | 128/200.14 |
| 5,235,969 A * | 8/1993 | Bellm .................. | 128/200.18 |
| 5,407,604 A * | 4/1995 | Luffman ..................... | 261/4 |
| 5,490,630 A | 2/1996 | Hecker | |

(Continued)

FOREIGN PATENT DOCUMENTS

| | | |
|---|---|---|
| EP | 1417982 A2 | 5/2004 |
| GB | 2055307 A | 3/1981 |

(Continued)

OTHER PUBLICATIONS

Meyer, Harriett, "Antibacterial Agent in Some Asthma Medications Linked to Airway Constriction, UF Scientists Find." UF News, Jan. 11, 2001, 2 pages.

(Continued)

*Primary Examiner* — Justine Yu
*Assistant Examiner* — Kathrynn Lyddane
(74) *Attorney, Agent, or Firm* — Hitchcock Evert LLP

(57) ABSTRACT

The invention relates to a small-volume nebulizer that is pre-filled with at least one unit-dose of medicine and hermetically sealed until use. The nebulizer may be sealed at the top with a removable cap that may be detached at the time of use and replaced with a patient connector. Likewise, the nebulizer may be sealed at the bottom with a bottom cap that is replaced with a gas source at the beginning of a therapeutic aerosol treatment.

23 Claims, 1 Drawing Sheet

(56) References Cited

U.S. PATENT DOCUMENTS

Figure 1:
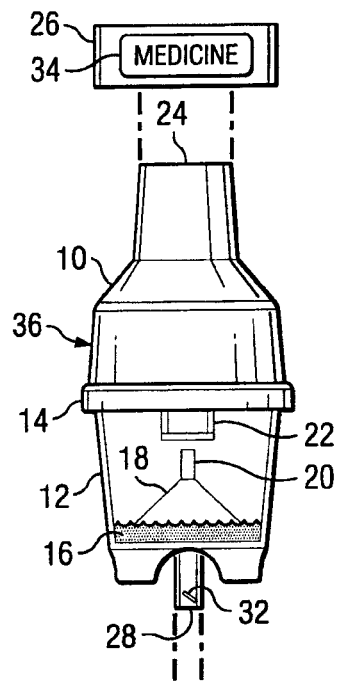

| | | | |
|---|---|---|---|
| 5,579,757 A * | 12/1996 | McMahon et al. | 128/200.21 |
| 5,584,285 A | 12/1996 | Salter et al. | |
| 5,752,502 A * | 5/1998 | King | 128/200.18 |
| 5,823,179 A * | 10/1998 | Grychowski et al. | 128/200.18 |
| 5,826,570 A | 10/1998 | Goodman et al. | |
| 5,864,097 A | 1/1999 | Alvino | |
| 6,044,841 A | 4/2000 | Verdun et al. | |
| 6,390,090 B1 | 5/2002 | Piper | |
| 6,632,842 B2 | 10/2003 | Chaundry et al. | |
| 6,722,364 B2 | 4/2004 | Connelly et al. | |
| 6,923,175 B2 | 8/2005 | Poole et al. | |
| 6,994,083 B2 * | 2/2006 | Foley et al. | 128/200.14 |
| 7,267,120 B2 | 9/2007 | Rustad et al. | |
| 8,539,951 B1 | 9/2013 | Meyer et al. | |
| 2001/0022279 A1 | 9/2001 | Denyer et al. | |
| 2004/0031485 A1* | 2/2004 | Rustad et al. | 128/200.18 |
| 2009/0050141 A1* | 2/2009 | King et al. | 128/200.18 |
| 2010/0095958 A1 | 4/2010 | King et al. | |

FOREIGN PATENT DOCUMENTS

| | | |
|---|---|---|
| JP | 08-508671 | 9/1996 |
| WO | WO 95/20989 | 8/1995 |
| WO | 02/055142 A2 | 7/2002 |
| WO | 03/080149 A2 | 10/2003 |
| WO | WO 2006/006963 A2 | 1/2006 |
| WO | WO 2008/144358 A1 | 11/2008 |

OTHER PUBLICATIONS

Grissiner, Matthew,RPh, FASCP, "Errors in the MakingL Nearly Unreadable Labeling of Plastic Ampules for Nebulizing Agents", Medication Errors, P&T Journal, May 2005, vol. 30, No. 5, pp. 255-258.

O'Malley, Catherine A. et al., "A Day in the Life of Nebulizer: Surveillance for Bacterial Growth in Nebulizer Equipment of Children with Cystic Fibrosis in the Hospital Setting", Respiratory Care 2007, Mar. 2007, vol. 52, No. 3, pp. 258-262.

U.S. Department of Health and HUman Services, Food and Drug Administration, Center for Drug Evaluation and Research (CDER), Center for Biologics Evaluation and Research (CBER) "Guidance for Industry, Container Closure Systems for Packaging Human Drugs and Biologics, Questions and Answers", May 2002, 6 pages.

Applyby,Julie, USA Today,DuoNeb®, "I Will Breathe Easier. Safety Concerns Grow Over Pharmacy-Mixed Drugs", 2005, 5 pages.

PCT International Search Report dated Sep. 29, 2008 for PCT/US08/63641.

Official Action issued in Japanese Patent Application No. 2010-508563, Mailing No. 641891, dated Sep. 21, 2012, and Translation (5 pages).

Hoisington ER, Chatburn RL, Stoller JK, Respiratory Institute, Cleveland Clinic Foundation, Cleveland, OH, A Comparison of Respiratory Care Workload With 2 Different Nebulizers., Abstract, PubMed, Respir Care, 2009, 1 page.

Chatburn RL, McPeck M., Section of Respiratory Care, Cleveland Clinic, Cleveland, OH, A New System for Understanding Nebulizer Performance., Abstract, PubMed, Respir Care, 2007, 1 page.

Jamalvi SW, Raza SJ, Naz F, Shamim S, Jamalvi SM., Department of Pediatrics, Jinnah Medical and Dental College, Karachi, Management of Acute Asthma in Children Using Metered Dose Inhaler and Small Volume Nebulizer., Abstract, PubMed, J Pak Med Assoc 2006, 1 page.

Colin Reisner, MD; Joseph Lee, RPh; Arthur Kotch, MD; and Gregory Dworkin, MD, Comparison of Volume Output from Two Different Continuous Nebulizer Systems, Annals of Allergy, Asthma & Immune, vol. 76, Feb. 1996, pp. 209-213.

Robert M. Kacmarek, Humidity and Aerosol Therapy, Chapter 71, Foundations of Respiratory Care, 1992, pp. 793-824, Churchill Livingstone Inc., New York, New York.

James B. Fink, MS, RRT, FAARC and Rajiv Dhand, MD, Respiratory Care Clinics of North America, Aerosol Therapy, Jun. 2001, pp. 131-340, vol. 7, No. 2, W.B. Saunders Company, A Harcourt Health Sciences Company, Philadelphia, Pennsylvania.

Bruce K. Rubin, MEng, MD, and James B. Fink MS, RRT, FAARC, Aerosol Therapy for Children, Respiratory Care Clinics of North America, Aerosol Therapy, Jun. 2001, pp. 175-213, vol. 7, No. 2, W.B. Saunders Company, A Harcourt Health Sciences Company, Phildelphia, Pennsylvania.

* cited by examiner

PRE-FILLED, SMALL-VOLUME NEBULIZER

FIELD OF THE INVENTION

The invention relates to a small-volume nebulizer that is pre-filled with medicine and hermetically sealed until use.

BACKGROUND OF THE INVENTION

It is estimated that more than thirty million people each year are treated for respiratory diseases such as asthma and cystic fibrosis by aerosolizing medication in disposable, small-volume nebulizers, following which the medicine is then inhaled by a patient as a part of the patient's therapy. Bronchodilators, such as albuterol sulfate or ipratropium bromide, are typically used in order to improve airflow among patients with pulmonary maladies. Additional medicines, used in different forms of therapy or to treat different maladies, are also possible. As used herein, the terms "medicine" and "medication" shall refer to any one or a combination of substances used primarily in patient treatment and specifically excluding substances such as saline solution or water used primarily for the humidification of gases inhaled by a patient.

Pharmaceutical companies originally packaged these medicines in containers that held multiple doses. In order to initiate a patient treatment, the medicine needed to be transferred from the container to the treatment equipment such as a nebulizer. As the containers were repeatedly opened and closed, the medicine was exposed to bacterial contamination. In order to stem bacterial growth, chemicals such as benzalkonium chloride, or BAC, were added. However, it was eventually found that BAC itself may lead to airway constriction. See, Meyer, Harriet, "*Antibacterial Agent In Some Asthma Medications Linked To Airway Constriction, UF Scientists Find.*" UF News, Jan. 11, 2001. Thus, the use of BAC may have negated or at least reduced any positive effect the bronchodilators may have had.

In order to reduce bacterial contamination without adding potentially harmful antibacterial chemicals, pharmaceutical manufacturers began to package respiratory drugs in single-dose or "unit-dose" containers, thus removing the need to repeatedly open a container of medicine to dispense a dose. These unit-dose respiratory drugs are typically packaged in soft plastic containers often formed from low density polyethylene, or LDPE, in order to help control costs and to make the containers easy to open.

Typically, the medication is opened by twisting the top of the unit-dose container until the plastic gives way at a thin portion of plastic at the neck. The medication is then transferred into a disposable nebulizer by aiming the unit-dose container opening at the nebulizer housing opening, squeezing the soft plastic of the container until the contents have emptied, and then disposing of the empty unit-dose container.

However, unit-dose packaging was found to have inherent drawbacks. First, packaging costs increased over the previous bulk packaging due to the fact that each dose necessitated its own container. Second, the mere fact that the medicine must be transferred from a packaging container to a nebulizer or other treatment device is believed to carry an inherent risk of contamination. Further, it was found that LDPE is permeable to chemicals that have moderate to high vapor pressure, such as adhesives, varnishes, inks, and solvents, all of which are typically used in labeling and packaging materials. After it was determined that a number of different inhalation drugs packaged in LDPE unit-dose containers were contaminated with these chemicals, the industry moved away from printed paper-and-ink labels to embossed labeling with raised lettering. See, Grissinger, Matthew, "*Errors in the Making: Nearly Unreadable Labeling of Plastic Ampules for Nebulizing Agents.*" Medication Errors; P&T Journal May 2005; Vol. 30, No. 5, pp. 255-258.

Unfortunately, medication errors due to the poor legibility of embossed lettering on LDPE unit-dose containers have caused great concern in the medical community. See, Grissinger, Id. Drug names, concentrations, lot numbers, and expiration dates are embossed into the containers in the form of transparent, raised letters rendering them virtually impossible to read. This leads all too frequently to administering the wrong drug. Mistakes occur when unit-dose respiratory drugs are stored in refrigerated "respiratory bins" where a number of different drugs are typically placed. The risk of using the wrong medication is also increased when clinicians keep various unit-dose medications in their laboratory coat pockets, which is often the case.

The problem of potential medication errors associated with embossed labeling on unit-dose containers continues. Transferring medication from unit-dose containers takes time, adds to difficulty of use, introduces the potential for contamination during transfer, and runs the risk of under-dosing due to spillage. In addition, there still remains the added packaging cost associated with packaging each dose separately, not to mention environmental concerns associated with the disposal of millions of plastic unit-dose containers. Finally, even though LDPE plastic containers are more malleable than other plastics, these containers are still difficult to open, especially for elderly and arthritic patients.

Thus, there remains a need for packaging system for liquid medicines, which may be clearly labeled without risk of label-chemical contamination, which reduces the risk of contamination during transfer of medication from container to nebulizer, which reduces or eliminates the cost associated with each dose needing its own individual container, which saves the time associated with transferring medication from container to nebulizer, which reduces the need for disposal of millions of plastic unit-dose containers, which reduces the risk of under-dosing due to spillage, and which may still be more easily opened or used by elderly and arthritic patients.

Medical nebulizers are divided into two general categories: 1) large-volume, and 2) small-volume. Large-volume nebulizers are used, most often in hospital settings, to humidify gas, usually oxygen, to a patient. Large-volume nebulizers are utilized to add moisture to otherwise very dry gas by aerosolizing water, usually sterilized water with some mixture of saline in order to mimic the human body's salt content. Large-volume nebulizers often come pre-filled with various mixtures of sterile water and saline.

Small-volume nebulizers, also referred to as "hand-held nebulizers," are used for delivering medication to the lungs. These devices are used for aerosolized medication therapy in both home and hospital settings. Although small-volume nebulizers are utilized in the delivery of a number of medications from analgesics to antibiotics, they are most often used to administer bronchodilators.

Small-volume nebulizers have come under scrutiny in recent years because of bacterial contamination. Traditionally, it has been common practice to clean and re-use disposable, single-patient-use, small-volume nebulizers. However, unless the nebulizer is completely sterilized it has been found that these "cleaned" nebulizers run the risk of growing such pathogens as *Pseudomonas aeruginosa, Staphylococcus aureus*, and *Haemophilus influenzae*, as well as other dangerous organisms. It is believed that contamination of the nebulizer occurs not only in spite of the cleaning, but may indeed be due to the cleaning itself. It is thought that poor cleaning techniques, inadequate drying, and the use of potable water sources may contribute to the contamination. Because of the risk of contamination and the fact that small-volume nebulizers are relatively inexpensive, especially when compared to the cost of nosocomial infections, many hospitals have come to the conclusion that it is safer and more prudent to dispose of the small-volume nebulizer soon after use. For example, it is currently a practice in many hospitals to utilize the same disposable nebulizer for twenty-four hours without cleaning, and then to dispose of it. See, O'Malley, Catherine A, et al. "*A Day in the Life of a Nebulizer: Surveillance for Bacterial Growth in Nebulizer Equipment of Children With Cystic Fibrosis in the Hospital Setting*." Respiratory Care 2007, Vol. 52, No. 3, pp. 258-262.

SUMMARY OF THE INVENTION

The present invention is a small-volume nebulizer prefilled with medication so that the nebulizer may also serve as a medication container. It is comprised of a small-volume nebulizer containing medication, hermetically sealed, with removable caps at the top and bottom ports.

Accordingly, an object of the present invention is to increase ease of use and save time by eliminating a step in the procedure of administering aerosol medication.

Another object of the present invention is to eliminate or reduce the costs associated with both disposable medicine containers and disposable nebulizers.

Another object of the present invention is to eliminate or reduce the likelihood of contaminating medication during transfer of medication from a storage container to a treatment device such as a nebulizer.

Another object of the present invention is to reduce the environmental burden associated with the disposal of unit-dose plastic containers and disposable nebulizers.

Another object of the present invention is to reduce medication identity and volume dosing errors.

Another object of the present invention is to reduce under-dosing due to spillage.

Another object of the present invention is to increase the ease of opening medicine containers.

Another object of the present invention is to reduce storage space required for both respiratory medications and small-volume nebulizers.

Additional aspects, advantages and features of the present invention are included in the following description of exemplary examples thereof, which description should be taken in conjunction with the accompanying figures, wherein like numerals are used to describe the same feature throughout the figures. All patents, patent applications, articles and other publications referenced herein are hereby incorporated herein by this reference in their entirety for all purposes.

A BRIEF DESCRIPTION OF THE DRAWINGS

FIG. 1 is a side view of the pre-filled, small-volume nebulizer of present invention.

FIG. 2 is a side view of an alternate embodiment of the pre-filled, small-volume nebulizer of present invention with a piercable outlet port cap, a one-way valve at the outlet port, a plurality of pre-filled unit-doses of medication, and unit-dose completion demarcation marks.

FIG. 3 is a side view of an alternate embodiment of the pre-filled, small-volume nebulizer of the present invention containing a separation compartment for a first component of a multi-component medication housed in the outlet port cap, and a second component of a multi-component medication housed in the nebulizer housing.

DETAILED DESCRIPTION

FIG. 1 shows a side view of a preferred embodiment of the pre-filled, small-volume nebulizer of present invention. Each component depicted herein may be fabricated by means of injection molding of a plastic compound, of such material as polypropylene or other plastic compound with appropriate properties for housing medication and fabricating a nebulizer. The pre-filled, small-volume nebulizer may be comprised of a housing top 10, a housing bottom 12, a housing seal 14, pre-filled unit-dose of medication 16, a siphon 18, a jet 20, a baffle 22, an outlet port 24, an outlet port cap 26, an inlet port 28, an inlet port cap 30, an inlet one-way valve 32, an outlet port cap medication label 34.

The general structure and assembly of small volume nebulizers is known in the art. Housing top 10, housing bottom 12, siphon 18, jet 20, baffle 22, outlet port 24, and inlet port 28 are generally cylindrical or conical in shape and are generally co-axial with one another. Baffle 22 and outlet port 24 are typically formed as a part of housing top 10, while inlet port 28 is typically formed as a part of housing bottom 12. Typically, siphon 18 and jet 20 will be formed together in a single piece, with the resulting piece placed inside housing bottom 12. In typical prior art nebulizers, housing top 10 and housing bottom 12 are detachably joined by a threaded connection or by a press fit.

In the nebulizer of the present invention, prior to joining housing top 10 and housing bottom 12, all components of the nebulizer may be sterilized. Once the unit has been sterilized, medication 16 may be introduced into housing bottom 12. Finally, housing top 10 is connected to housing bottom 12 at housing seal 14, which is hermetically sealed by glue, sonic welding, or other known sealing techniques, to form nebulizer body 36.

To begin a medication therapy session with the pre-filled, small-volume nebulizer the patient or clinician may observe outlet port cap medication label 34 in order to verify the proper medicine is being used. Outlet port cap 26 may be removed, discarded, and replaced with either a mouthpiece attachment or some other type of patient interface common to the industry. To facilitate use of standard patient interface devices, outlet port 24 is of a shape, dimension and/or configuration commonly used in the industry. More specifically, outlet port 24 is preferably a generally cylindrical, tube having an outside diameter of between 15 and 30 millimeters, preferably between 20 and 25 millimeters, and most preferably of approximately 22 millimeters. Inlet port cap 30 may be removed and a source of gas under pressure such as an oxygen tube is connected to the inlet. During these maneuvers, pre-filled unit-dose of medication 16 within the nebulizer is prevented from exiting through inlet port 28 by one-way valve 32. As the therapy begins, gas under pressure enters inlet port 28 and travels through siphon 18 creating an area of relatively low pressure, which entrains at least a portion of pre-filled unit-dose of medication 16. The gas/medication mixture exits through jet 20, which directs the mixture such that it impinges against baffle 22 where the liquid medicine is broken up into small aerosol particles. The aerosol exits outlet port 24 and is delivered to the patient through a patient interface (not shown).

FIG. 2 depicts a side view of an alternate embodiment of the pre-filled, small-volume nebulizer of the present invention. In this embodiment outlet port 24 is sealed by piercable outlet port cap 38, which may either be removed or may be pierced at the time of use. In a preferred embodiment, the patient interface may be equipped with a mechanical appendage such as a spike which may be used to pierce outlet port cap 38 such that pre-filled unit-dose of medication 16 may be accessed without an operator or patient touching outlet port 24, thereby further reducing the likelihood of contamination. Furthermore, patient interface (not shown) may comprise a mouthpiece connected to a mouthpiece "T" which contains a spike for the purpose of saving time in the procedure of preparing for a therapy session. Outlet port 24 also contains an outlet port one-way valve 40, which allows aerosolized medication to flow out, but prevents retrograde flow in order to help defend against contamination.

Figure 2:
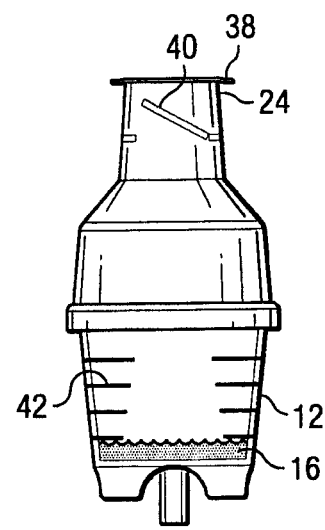

The embodiment depicted in FIG. 2 further displays an alternate embodiment of the medication contained in the nebulizer. Specifically, in the embodiment depicted in FIG. 2, housing bottom 12 contains a plurality of pre-filled unit-doses of medication 16, and unit-dose completion demarcation marks 42. By providing a nebulizer body 36 pre-filled with multiple unit-doses of medicine, this embodiment of the present invention allows a patient or clinician to utilize the device for a predetermined period of time, twenty-four hours for example, without cleaning and reusing, and without disposing of the device earlier than is needed to prevent contamination. Unit-dose completion demarcation marks 42, allow a patient or clinician to determine when the delivery of a unit-dose of medication is complete and stop the therapy until it is time for the next.

Figure 3:
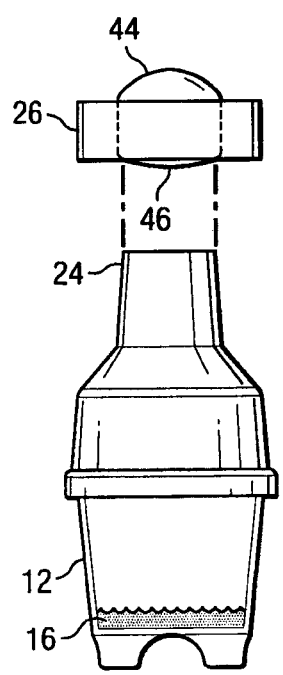

FIG. 3 is a side view of a further alternate embodiment of the pre-filled, small-volume nebulizer of the present invention. In this embodiment, a compartment is provided within outlet port cap 26 for keeping a first component of a multi-component medication separate from a second component of a multi-component medication until use. This embodiment may find greatest application when the medicine to be administered is a mixture of one or more components, for example the mixture of Albuterol Sulfate and Ipratropium Bromide. However, mixing of medications can lead to additional problems associated with improper dosing and contamination. In some instances, it is believed that the useable life of these medicines once mixed is undesirably short. Therefore, in practice a patient or clinician generally mixes the medicines immediately prior to treatment. Of course, the increased handling of the medicine by a patient or clinician required during mixing may increase the likelihood of contamination and/or improper dosing. Therefore, by providing a pre-filled nebulizer which can separate multiple medication components until treatment, this embodiment of the present invention may greatly reduce these risks.

As shown in FIG. 3, outlet port cap 26 includes medication separation compartment 44, which may house a first component of a multi-component medication to be mixed with at least a second component of a multi-component medication at the time of use. Medication separation compartment 44 may be fabricated from a soft, malleable plastic composition such as a formulation of low density polyethylene. At the bottom of medication separation compartment 44 is a medication separation outlet gate 46 which is formed by fabricating a weak or thin portion of the plastic. As pressure is exerted at the top of medication separation compartment 44, medication separation outlet gate 46 breaks open and deposits its contents into housing bottom 12 where it mixes with pre-filled unit-dose of medication 16.

What is claimed:

1. A pre-filled small-volume nebulizer ready for a patient to administer for respiratory care comprising:
    a small-volume nebulizer body comprising a housing bottom, a housing top and a hermetic seal created between said housing bottom and said housing top, wherein contained within said small-volume nebulizer body is at least one of a siphon, a jet, and a baffle;
    an outlet opening;
    a first cap removably engaged with said outlet opening;
    an inlet opening;
    a second cap removably engaged with said inlet opening;
    a unit-dose of medication contained within said small-volume nebulizer body.

2. The pre-filled, small-volume nebulizer according to claim 1, further comprising a means for preventing egress of said unit-dose of medication through said inlet opening.

3. The pre-filled, small-volume nebulizer according to claim 1, wherein said unit-dose of medication is a first component of a multi-component medication, and said apparatus further includes a first compartment containing a second component of said multi-component medication.

4. The pre-filled, small-volume nebulizer according to claim 1, further comprising one or more labels identifying said unit dose of medication.

5. The pre-filled, small-volume nebulizer according to claim 1, further comprising a means of preventing retrograde movement into said nebulizer housing.

6. The pre-filled, small-volume nebulizer according to claim 1, further comprising a plurality of said unit-doses of medication.

7. The pre-filled, small-volume nebulizer according to claim 6, further comprising unit-dose completion demarcation marks.

8. The pre-filled, small-volume nebulizer according to claim 1, wherein said first cap is comprised of a piercable seal.

9. The pre-filled, small-volume nebulizer according to claim 1, wherein said outlet-opening is cylindrical.

10. The pre-filled, small-volume nebulizer according to claim 1, wherein said hermetic seal, said first cap and said second cap prevent said unit-dose of medication from spilling from said small-volume nebulizer body.

11. A small-volume, pre-filled nebulizer ready for a patient to administer for respiratory care comprising:
    a small-volume nebulizer body, wherein contained within said small-volume nebulizer body is at least one of a siphon, a jet, and a baffle;
    an outlet opening;
    a first cap removably engaged with and sealing said outlet opening;
    an inlet opening;
    a second cap removably engaged with and sealing said inlet opening;
    a plurality of unit-doses of medication sealed within said small-volume nebulizer body.

12. The small-volume, pre-filled nebulizer according to claim 11, further including a means for preventing egress of said unit-dose of medication through said inlet opening.

13. The small-volume, pre-filled nebulizer according to claim 11, wherein said plurality of unit-doses of medication are a plurality of first components of a multi-component medication, and said apparatus further includes a first compartment containing a plurality of unit-doses of a second component of said multi-component medication.

14. The small-volume, pre-filled nebulizer according to claim 11, further comprising one or more labels identifying said plurality of unit-doses of medication.

15. The small-volume, pre-filled nebulizer according to claim 11, further comprising a means of preventing retrograde movement into said small-volume nebulizer housing.

16. The small-volume, pre-filled nebulizer according to claim 11, further comprising unit-dose completion demarcation marks.

17. The small-volume, pre-filled nebulizer according to claim 11, wherein said first cap is comprised of a piercable seal.

18. The small-volume, pre-filled nebulizer according to claim 11 wherein said outlet opening is cylindrical.

19. The small-volume, pre-filled nebulizer according to claim 11, wherein said small-volume nebulizer body comprises a housing bottom, a housing top and a hermetic seal created between said housing bottom and said housing top.

20. A method of administering aerosolized medicine utilizing a small-volume nebulizer pre-filled with medicine ready for a patient to administer comprising the steps of:
providing said small-volume nebulizer, pre-filled with at least one unit-dose of medicine sealed within said small-volume nebulizer, wherein contained within said small-volume nebulizer is at least one of a siphon, a jet, and a baffle;
removing an outlet cap removably engaged with said small-volume nebulizer;
replacing said outlet cap with a patient interface;
removing an inlet cap removably engaged with said small-volume nebulizer;
connecting a source of gas under pressure to said small-volume nebulizer;
delivering aerosolized medicine to a patient.

21. The method of claim 20 wherein said nebulizer further comprises pre-filled first and second compartments containing first and second components of a multi-component medicine, further comprising the step of breaking open at least said first compartment to cause mixing of said first and second components of a multi-component medicine.

22. The method of claim 20 wherein said small-volume nebulizer includes a medication label affixed to said small-volume nebulizer which identifies said at least one unit-dose of medicine contained within said small-volume nebulizer.

23. The method of claim 20 wherein said inlet cap is removably engaged with an inlet opening of said small-volume nebulizer and said source of gas under pressure is connected to said inlet opening of said small-volume nebulizer.

* * * * *

UNITED STATES PATENT AND TRADEMARK OFFICE
CERTIFICATE OF CORRECTION

PATENT NO. : 9,849,254 B2
APPLICATION NO. : 11/748907
DATED : December 26, 2017
INVENTOR(S) : Joseph Dee Faram Page 1 of 1

It is certified that error appears in the above-identified patent and that said Letters Patent is hereby corrected as shown below:

Column 6, Lines 20-21: Claim 3, delete "apparatus" and insert --pre-filled, small-volume nebulizer--

Column 6, Line 25: Claim 4, delete "unit dose" and insert --unit-dose--

Column 6, Line 28: Claim 5, delete "housing" and insert --body--

Column 6, Line 39: Claim 8, delete "outlet-opening" and insert --outlet opening--

Column 6, Line 59: Claim 12, delete "unit-dose of medication" and insert --plurality of unit-doses of medication--

Column 6, Line 63: Claim 13, delete "apparatus" and insert --small-volume, pre-filled nebulizer--

Column 7, Line 6: Claim 15, delete "housing" and insert --body--

Signed and Sealed this
Tenth Day of July, 2018

Andrei Iancu
*Director of the United States Patent and Trademark Office*